(12) United States Patent
Palasis

(10) Patent No.: US 7,179,251 B2
(45) Date of Patent: Feb. 20, 2007

(54) THERAPEUTIC DELIVERY BALLOON

(75) Inventor: Maria Palasis, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 09/760,807

(22) Filed: Jan. 17, 2001

(65) Prior Publication Data
US 2002/0095114 A1 Jul. 18, 2002

(51) Int. Cl.
A61M 29/00 (2006.01)

(52) U.S. Cl. .................. 604/509; 604/919; 604/101.02

(58) Field of Classification Search ............. 604/93.01, 604/96.01, 97.01, 101.01–101.03, 102.01, 604/103.01–103.02, 103.05–103.06, 103.11, 604/103.08; 606/915, 919, 192, 194
See application file for complete search history.

(56) References Cited

U.S. PATENT DOCUMENTS

| 4,338,942 | A | * | 7/1982 | Fogarty ..................... 606/194 |
| 4,649,914 | A | * | 3/1987 | Kowalewski ........... 128/207.15 |
| 4,983,167 | A | * | 1/1991 | Sahota ........................ 606/194 |
| 4,994,033 | A | * | 2/1991 | Shockey et al. ........ 604/101.02 |
| 5,102,402 | A | * | 4/1992 | Dror et al. ............. 604/103.02 |
| 5,213,576 | A | * | 5/1993 | Abiuso et al. ......... 604/101.02 |
| 5,286,254 | A | * | 2/1994 | Shapland et al. ...... 604/103.01 |
| 5,295,962 | A | * | 3/1994 | Crocker et al. ........ 604/101.02 |
| 5,304,121 | A | * | 4/1994 | Sahatjian ..................... 604/509 |
| 5,472,424 | A | * | 12/1995 | Lampropoulos et al. . 604/97.03 |
| 5,588,962 | A | * | 12/1996 | Nicholas et al. ............ 604/507 |
| 5,662,609 | A | * | 9/1997 | Slepian ................... 604/101.03 |
| 5,704,913 | A | * | 1/1998 | Abele et al. ........... 604/101.02 |
| 5,707,358 | A | * | 1/1998 | Wright .................... 604/103.07 |
| 5,785,694 | A | * | 7/1998 | Cohen et al. ................ 604/250 |
| 5,868,776 | A | * | 2/1999 | Wright ........................ 606/194 |
| 5,980,531 | A |   | 11/1999 | Goodin et al. |
| 6,048,332 | A |   | 4/2000 | Duffy et al. |
| 6,129,706 | A |   | 10/2000 | Janacek |
| 6,132,397 | A | * | 10/2000 | Davis et al. ............ 604/101.02 |
| 6,136,011 | A |   | 10/2000 | Stambaugh |
| 6,146,358 | A | * | 11/2000 | Rowe ..................... 604/103.02 |
| 6,471,672 | B1 | * | 10/2002 | Brown et al. .......... 604/101.01 |
| 6,786,889 | B1 |   | 9/2004 | Musbach et al. |

FOREIGN PATENT DOCUMENTS

EP 0 835 673 4/1998
EP 0835673 A2 * 4/1998

* cited by examiner

Primary Examiner—LoAn H. Thanh
(74) Attorney, Agent, or Firm—Kenyon & Kenyon LLP

(57) ABSTRACT

The present invention regards a therapeutic delivery balloon and includes a system for delivering therapeutic to an irregular interior vessel surface. This system includes a catheter having a proximal end, a distal end, and an internal lumen; a source of fluid in communication with the internal lumen of the catheter; and, a first inflatable balloon having an exterior surface, wherein the balloon is hyper-deformable, is in communication with the internal lumen of the catheter, and has an exterior surface in communication with a therapeutic when the balloon is in expanded state.

12 Claims, 7 Drawing Sheets

THERAPEUTIC DELIVERY BALLOON

TECHNICAL FIELD

The present invention regards the delivery of therapeutic to a target site of an organic vessel. More particularly the present invention regards the delivery of therapeutic to the interior walls of a lumen via a hyper-deformable inflatable balloon placed within the lumen.

BACKGROUND OF THE INVENTION

The delivery of therapeutic to the interior lumen walls of a diseased vessel is an important, often repeated, procedure in the practice of modern medicine. The delivery of the therapeutic can be completed through the use of numerous devices and procedures including direct injection by syringe and needle, pneumatic injection of the therapeutic into the diseased tissue, and the release of the therapeutic, near the target site, by the distal end of a catheter inserted into the lumen. When the diseased or otherwise targeted area is irregularly shaped its unorthodox shape can retard the effective and uniform delivery and absorption of the therapeutic at the target site. For example, as can be seen in FIG. 1, which depicts a drug delivery bladder 13 being used to place therapeutic against the interior walls of lumen 12 in vessel 10, the walls of the bladder 13 do not touch all of the walls of the lumen 12. As can be seen the vessel 10 contains a calcification 11 that acts to distort the configuration of lumen 12. Previously round, the lumen 12 has been distorted into a reniform configuration due to the disforming forces of the calcification 11. Accordingly, when the bladder 13, located on the distal end of a catheter 14 is inflated, only a portion of the bladder's 13 exterior surface comes in contact with the interior wall of the lumen 12 and, thus, only this contacted portion can be directly reached by the therapeutic. Likewise, when the wall of the lumen 12 has a cratered or otherwise irregular profile, which is typical in arteries inflicted with arteriosclerosis, the expanding bladder is unable to contact the entire surface area of the wall of the lumen 12. When this occurs, therapeutic being delivered is sporadically and unevenly placed at the target site, leaving portions of the lumen wall unexposed to the therapeutic. FIG. 1a provides an illustrative enlarged example of an interface between a bladder surface 15 and an irregularly shaped lumen wall 16. As is evident, certain craters 17 of the lumen wall 16 are not in contact with the bladder surface 15. Therefore, irregularly shaped lumen walls present an impediment to and a retarding factor in the delivery of therapeutic to the irregularly shaped lumen walls.

SUMMARY OF THE INVENTION

The present invention regards a therapeutic delivery balloon. In one embodiment a system for delivering therapeutic to an irregular interior vessel surface is provided. This system includes a catheter having a proximal end, a distal end, and an internal lumen; a source of fluid in communication with the internal lumen of the catheter; and, a first inflatable balloon having an exterior surface, wherein the balloon is hyper-deformable, is in communication with the internal lumen of the catheter, and has an exterior surface in communication with a therapeutic when the balloon is in an expanded state.

In an alternative embodiment of the present invention a method for delivering therapeutic to an irregular interior vessel surface of a patient is provided. This method includes: inserting an expandable hyper-deformable membrane into the vessel of the patient, the expandable hyper-deformable membrane having an exterior surface; positioning the expandable hyper-deformable membrane at an irregular interior surface of the vessel within the patient; and, forcing fluid into the expandable hyper-deformable membrane to expand the expandable hyper-deformable membrane, the expandable hyper-deformable membrane becoming juxtaposed to the irregular interior surface of the vessel of the patient.

DETAILED DESCRIPTION

Figure 1:
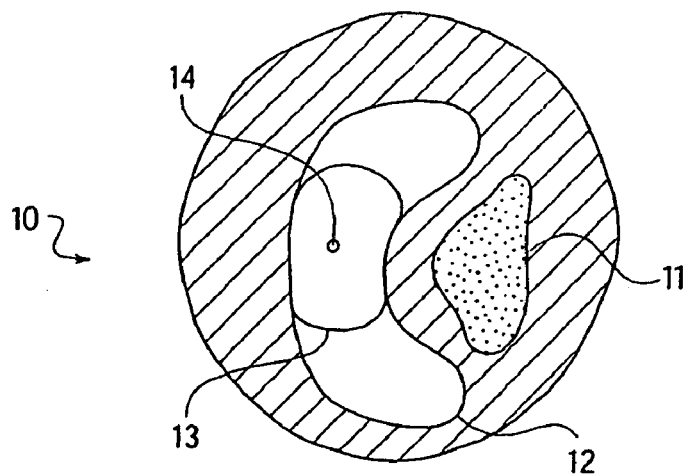
FIG. 1 is a cross-sectional view of an expandable bladder located within an irregularly shaped lumen of a vessel.
Figure 1A:
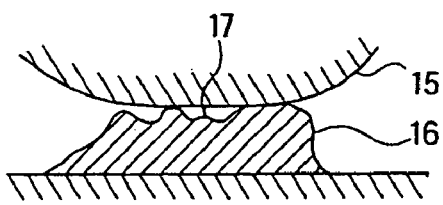
FIG. 1a is an enlarged cross-sectional view of an interface point between an expandable bladder and an irregularly shaped lumen wall.
Figure 2:
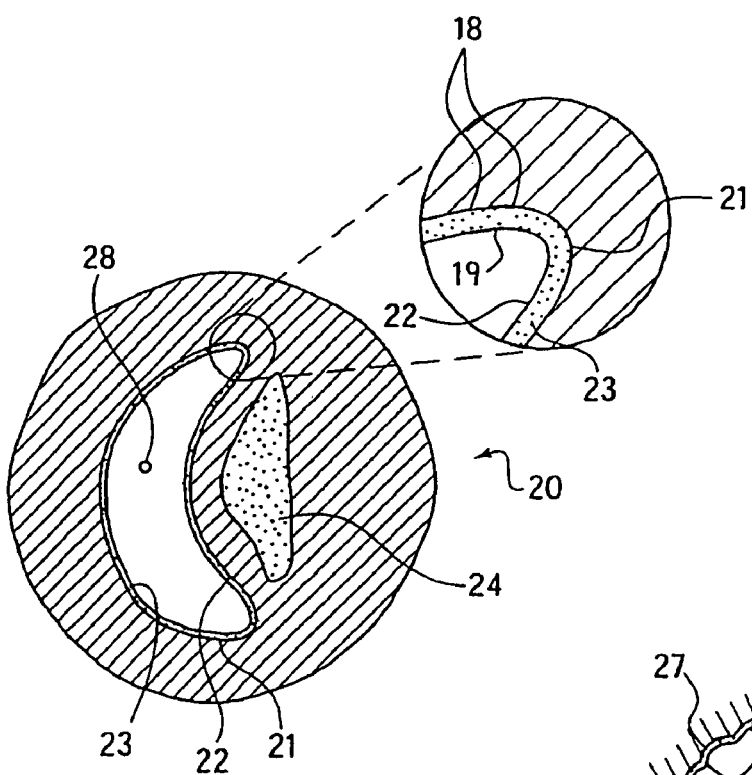
FIG. 2 is a cross-sectional view of an expanded hyper-deformable inflatable balloon within an irregularly shaped lumen of a vessel in accordance with an embodiment of the present invention.

FIG. 2 is an enlarged cross-sectional view of a vessel 20, having a lumen, located within the body of a patient. The vessel 20 contains reniform interior lumen wall surface 21. As can be seen, this interior lumen wall surface 21 is shaped in an irregular configuration due to the calcification 24 located within the wall of the vessel 20. This calcification 24 places pressure on the interior lumen wall surface 21, causing it to deform into its irregular shape.

Also depicted in FIG. 2 is a hyper-deformable inflatable balloon 22. This balloon 22, which is shown in its inflated state, is mounted on the distal end of catheter 28. Positioned between the lumen wall surface 21 and the hyper-deformable inflatable balloon 22 is a therapeutic 23. The therapeutic 23 may be used to treat, regenerate, or otherwise affect the interior lumen wall surface 21 or the vessel wall itself. The proximity of the hyper-deformable inflatable balloon 22, the interior lumen wall surface 21, and the therapeutic 23 is clearly shown in the enlarged portion of FIG. 2.

As can be seen in the enlarged portion of FIG. 2, the hyper-deformable inflatable balloon 22 closely mimics and contours to the interior lumen wall surface 21 such that the therapeutic 23 located on the exterior of the hyper-deformable inflatable balloon may be placed adjacent to and in contact with the interior lumen wall surface 21 by the exterior surface of the balloon 22. The term hyper-deformable as used herein includes materials that are capable of stretching or expanding in order to closely replicate the irregular surfaces with which they are expanded up against. Due to the hyper-deformability of the inflatable balloon 22, some areas of the balloon will stretch further from the catheter 28 than others. This is made evident in FIG. 2, which illustrates the varying distances from the catheter 28 that the balloon may travel.

The hyper-deformable inflatable balloon 22 may be made with any material that is hyper-deformable. Latex, silicone, polyurethane, rubber (including styrene and isobutylene styrene), and nylon, are each examples of materials that may be used in manufacturing the hyper-deformable balloon. Moreover, the actual configuration of the balloon may also make it hyper-deformable. For example, the balloon may be internally ribbed 18 or notched 19 or otherwise specifically configured to increase its deformability and, thus, make it readily conformable to its surroundings in an expanded state.

The vessel 20 may be any vessel located within or outside of the body of a patient. It may include blood-carrying vessels such as the veins, arteries, and chambers of the heart, it may also include the esophagus, the ureters, the intestines, the pockets of fluid located within the individual vertebrae of the spinal column and any other suitable vessel as apparent to one of skill in the art. Organs and tissues that may be treated by the methods of the present invention include any mammalian tissue or organ, whether located in vivo or ex vivo. Non-limiting examples include the heart, the lungs, the brain, the livers, the kidneys, the bladder, the intestines, the stomach, the pancreas, the ovaries, the prostate, the eyes, as well as tumors, cartilage and bone.

Figure 2A:
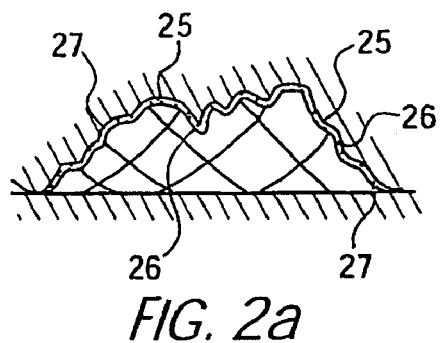
FIG. 2a is an enlarged cross-sectional view of a portion of a hyper-deformable inflatable balloon conforming to an irregularly shaped lumen wall in accordance with an alternative embodiment of the present invention.

FIG. 2a is an enlarged sectional view of the interface point of an inflated hyper-deformable inflatable balloon 25 conforming to an irregular surface of a vessel wall 26. As can be seen in FIG. 2a, the hyper-deformable inflatable balloon 25 has very closely conformed to the irregular surface of the vessel wall 26. Because the hyper-deformable inflatable balloon 25 is able to conform to the irregular surface of the vessel wall 26, the therapeutic 27, previously located on the outside surface of the balloon 25, may come in direct contact with the entire surface of the irregularly shaped vessel wall 26.

Figure 3:
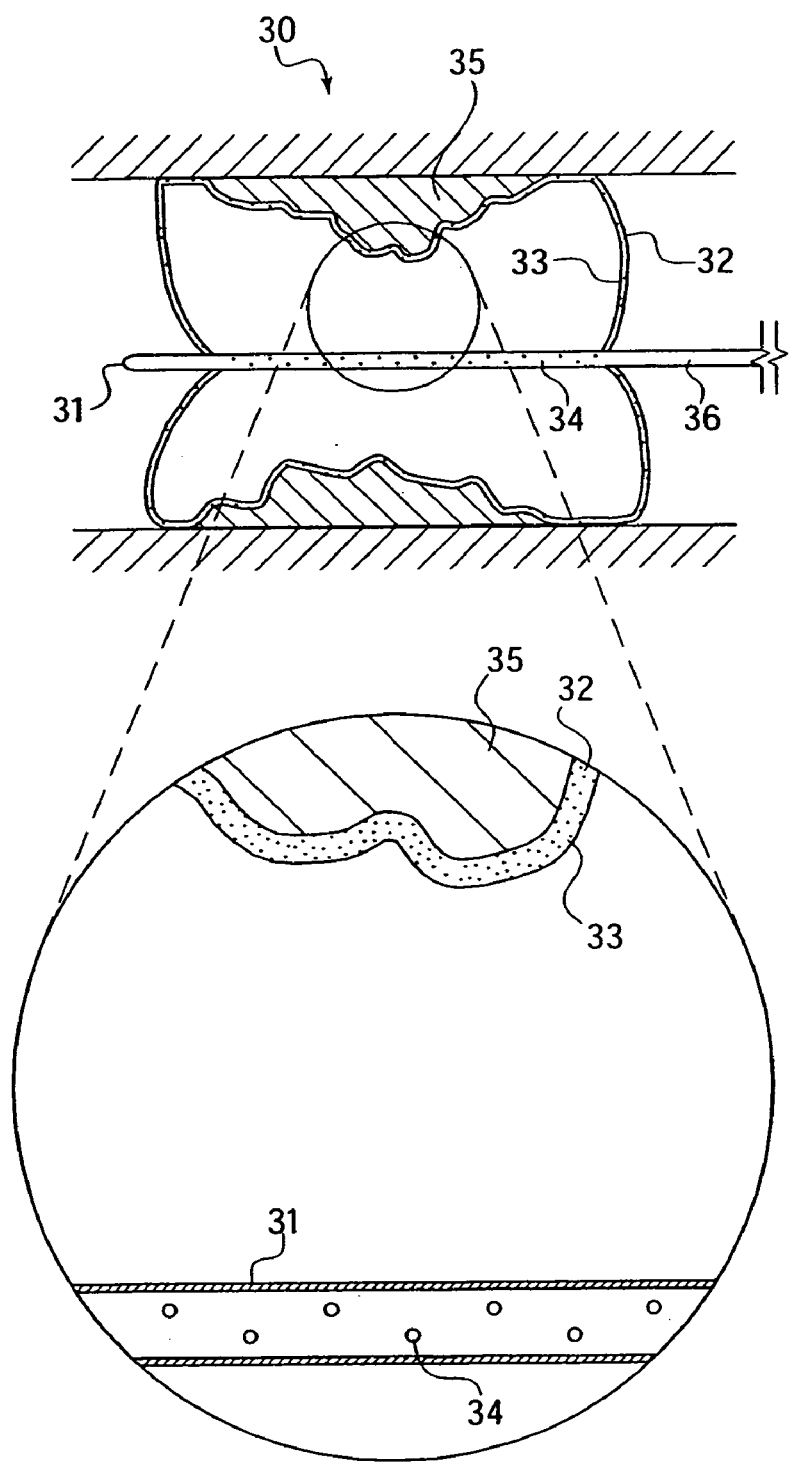
FIG. 3 is a cross-sectional view, with an enlarged portion, of a distal end of a catheter employing a hyper-deformable inflatable balloon as employed within an irregularly shaped lumen in accordance with another alternative embodiment of the present invention.

FIG. 3 illustrates an enlarged sectional view of the distal end of a catheter 31 located within a vessel 30 having an irregularly shaped lumen wall 35. The distal end of the catheter 31 is shown in FIG. 3 as being inserted past the irregular shaped lumen wall 35. As can be seen, the surface of the distal end of the catheter 31 contains a plurality of orifices 34 situated within and in fluid communication with the hyper-inflatable balloon 33. These orifices, while round, may be any configuration that provides for the exit of the fluid from inside of the catheter 31 to inside of the balloon 33. Also evident in this figure is a therapeutic 32, which has been previously placed on the exterior surface of the hyper-deformable inflatable balloon 33.

In use, bio-compatible non-compressible fluid will be pumped from the proximal end of the catheter 31 down a lumen in the catheter and out the orifices 34 of the catheter 31 to inflate the hyper-deformable inflatable balloon 33. The balloon 33, in this embodiment, inflates under the pressure of the fluid, being pumped out of the orifices 34, until the balloon 33 comes in contact with the irregularly shaped lumen wall 35. Due to the hyper-deformability of the balloon 33, the balloon 33 is able to conform to the irregularly shaped lumen wall 35 and, therefore, expose the irregularly shaped lumen wall 35 to the therapeutic 32 located on the outside of the hyper-deformable inflatable balloon 33.

The interface between the hyper-deformable inflatable balloon 33, the therapeutic 32, and the irregularly shaped lumen wall 35 is clearly shown in the enlarged circle of FIG. 3. As is evident in this embodiment, when the balloon 33 is inflated its hyper-deformability allows the therapeutic 32 to be placed adjacent to and in contact with the entire surface of the irregularly shaped lumen wall 35.

While the orifices 34 in FIG. 3 are illustrated as being evenly and uniformly spaced along the catheter 31, these orifices 34 may be of different sizes or different shapes and may be located at different spacings along the catheter. In a preferred embodiment, however, these orifices will be evenly spaced along the catheter 31 to facilitate the even distribution of fluid into the hyper-deformable inflatable balloon and, consequently, the even and uniform inflation of the balloon 33.

In this embodiment, the fluid may be pumped into the catheter through a syringe (which is illustrated in FIGS. 4–6, 13, and 15) located at the proximal end of the catheter or, alternatively, through any other pumping means that can apply a pressure on the fluid to carry it into the balloon. These alternative means could include a micro-pump, an inflator, and a collapsible bladder. In a preferred embodiment, the amount of fluid being injected into the catheter and/or the infusion pressure placed on the fluid, will be measured to help monitor the expansion of the balloon 33 within the vessel 30 and to preclude an overabundance of fluid from being injected into the balloon 33, causing the balloon 33 or the vessel 30 to unwantedly rupture. By measuring the amount of pressure placed on the fluid the operator can monitor the progress of the procedure. In this preferred embodiment, the amount of pressure generated in the vessel will not exceed a known tolerable pressure level for the vessel being treated. Lastly, due to the risk of rupture, it is preferred that any fluid used to expand the hyper-deformable inflatable balloon 33 be bio-compatible with the environment in which the hyper-deformable inflatable balloon 33 and catheter 31 are employed. These fluids can include contrast solutions such as those used in ultrasound, fluoroscopy, and MRI procedures as well as various brine solutions.

Figure 4:
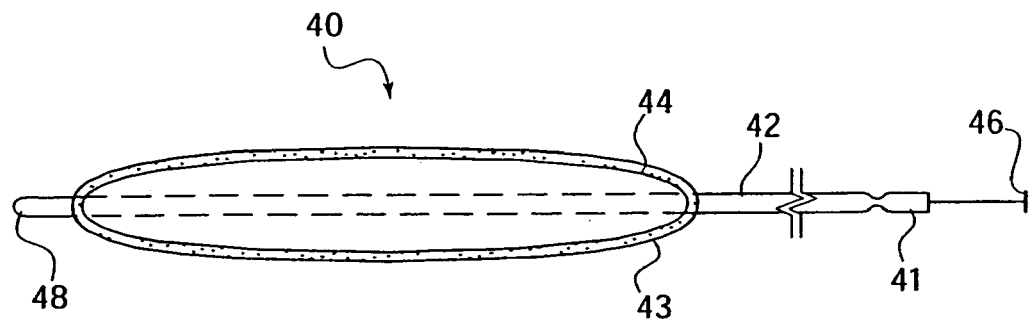
FIG. 4 is a side view of a distal end of a catheter employing a hyper-deformable inflatable balloon in accordance with another alternative embodiment of the present invention.

FIG. 4 is a side view of a catheter 40 in accordance with another alternative embodiment of the present invention. The distal tip 48, tube 42, syringe 41, plunger 46, therapeutic 43, and hyper-deformable inflatable balloon 44 of the catheter 40 are all clearly evident in FIG. 4. As can be seen and as discussed above, the syringe 41 has been attached to the proximal end of the catheter 40. This syringe 41 may contain a fluid that is injected and pushed down through the tube 42 of the catheter 40, by depressing the plunger 46, to inflate the balloon 44. Upon being inflated, therapeutic 43 may be placed adjacent to and in contact with an irregularly shaped lumen wall located near the distal end of the catheter 40. In this embodiment the therapeutic has been placed on the surface of the balloon 44 prior to the commencement of the medical procedure. Alternatively, as discussed below, the therapeutic 43 may also be pumped to the surface of the balloon before or during the completion of the procedure.

Figure 5:
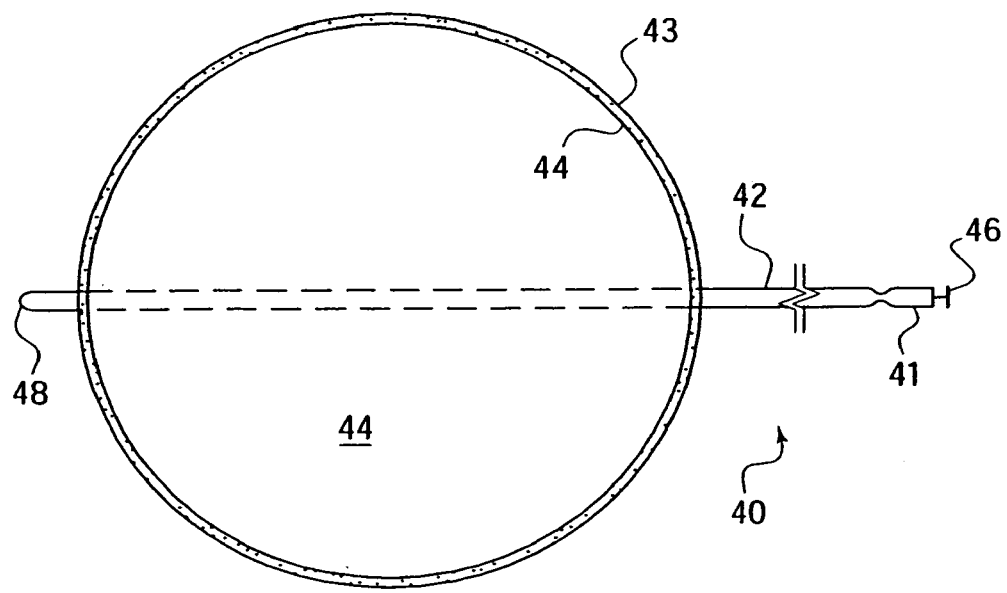
FIG. 5 is a side view of the hyper-deformable inflatable balloon of FIG. 4 in an inflated configuration.

FIG. 5 is a side view of the catheter from FIG. 4. As can be seen, the hyper-deformable inflatable balloon 44 is illustrated in an extended position. As is also evident, the plunger 46, previously shown in an extended position in FIG. 4, is shown in a compressed position in FIG. 5. As a result of depressing or compressing the plunger 46 from the first position to the second position, the hyper-deformable inflatable balloon 44 has been inflated. It will be evident to one of skill in the art that FIG. 5 is clearly not drawn to scale as the amount of fluid displaced by the movement of the plunger 46 would be smaller than the volume of the inflated balloon 44 illustrated in FIG. 5.

As mentioned above, the volume of fluid injected into the hyper-deformable inflatable balloon 44 may be measured and monitored during the procedure to control the rate and amount of balloon 44 inflation. This measurement may be completed by placing striations or markings along the side of the syringe 41 and then counting the number of markings that the plunger 46 has passed through. Alternatively, if another type of pump is used this pump may be calibrated to measure the amount of fluid injected into the lumen of the catheter, the amount of resistive force pushing back on fluid being pumped into the lumen or both. Moreover, the pump or any of the inflation devices, may be used to control the rate at which the balloon is expanded. Also, the tracing fluid described above, may be used in concert with an imaging device to track the progress of the expansion of the delivery balloon 44.

Figure 6:
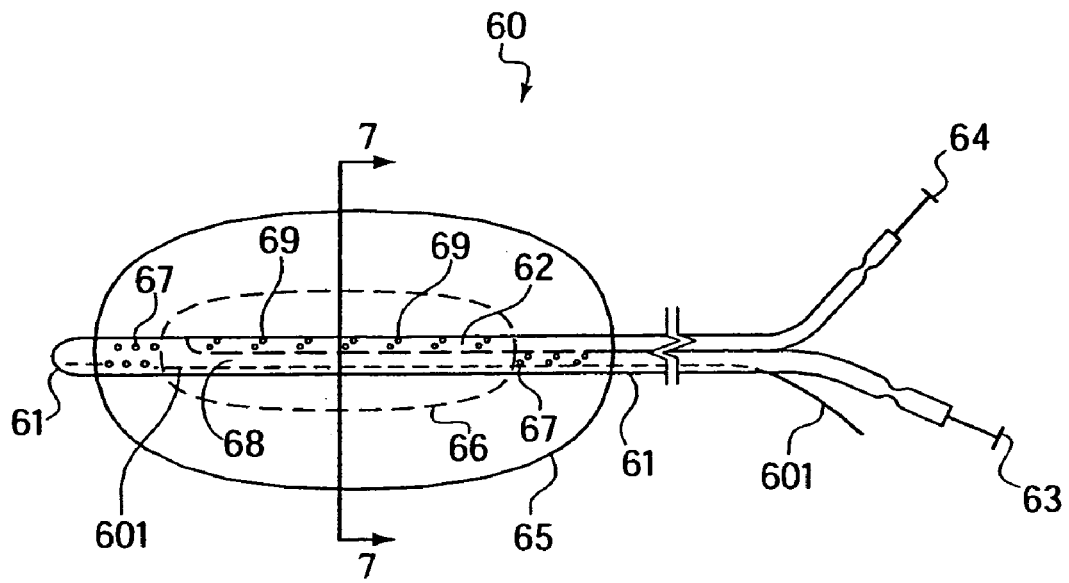
FIG. 6 is a side view of a catheter employing a dilating bladder and a hyper-deformable inflatable balloon in accordance with another alternative embodiment of the present invention.

FIG. 6 is a side view of another alternative embodiment of the present invention. In FIG. 6, a catheter 60 has a first syringe 64, a second syringe 63, and the end of guide wire 601 located at its proximal end and a hyper-deformable inflatable balloon 65 and a dilation bladder 66 located at its distal end. Also illustrated in FIG. 6 are the catheter body 61, the first lumen 62, the second lumen 68, orifices 67, and openings 69. The first syringe 64 may be in fluid communication with the first lumen 62 and the opening 69 in this embodiment. The second syringe 63 may be in fluid communication with the orifices 67 through the second lumen 68 in this embodiment. The first syringe 64 may be in fluid communication with the openings 69 through the first lumen 62 in this embodiment.

In use, when the distal end of the catheter 60 is placed within a lumen of the body through the use of the guide wire 601 the dilation bladder 66 may be inflated to first dilate the lumen and then, next, the hyper-deformable inflatable balloon 65 may be inflated to place therapeutic against the irregular but now dilated surface of the lumen. The openings 69 are located on the first lumen within the distillation bladder 66 such that when the first syringe 64 is depressed, fluid may be pumped into the dilation bladder 66 and the dilation bladder 66 will expand. Similarly, the orifices 67 may be located along the second lumen 68 and positioned such that when the second syringe 63 is depressed, the balloon 65 will be forced to expand.

As described above, fluid may be used to inflate both the bladder and the balloon, and the volume and rate of entry of this fluid may be monitored to help measure the progress of the procedure and to perform various maneuvers and steps of the delivery procedure.

Figure 7:
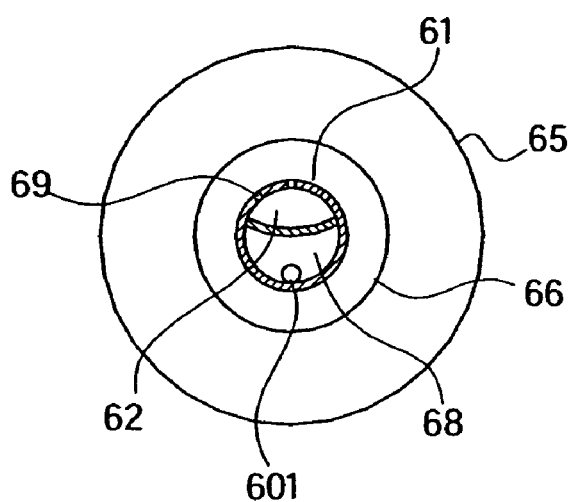
FIG. 7 is a sectional view taken along line 7—7 of FIG. 6.

FIG. 7 is a cross-sectional view taken along line 7—7 of FIG. 6. The first lumen 62, the second lumen 68, the openings 69, the catheter body 61, the dilation bladder 66, the guide wire 601, and the hyper-deformable inflatable balloon 65 are all clearly evident in this view. As can be seen, the openings 69 are evenly spaced along the catheter body 61. In addition, while three openings 69 are shown in this embodiment, other configurations of the openings may be employed, including varying the number of openings and openings of different shapes and sizes.

The catheter body 61 in this embodiment, as well as in the other embodiments, may be made from numerous materials, including stainless steel, plastic, and other suitably rigid polymers. It is preferable that the materials used are compatible with the target sites in which they can be used and that they may be able to withstand the pressures generated by the fluids passing through them. In addition, they should be flexible enough such that the catheter may be effectively snaked down through a vessel in the body having an irregularly shaped lumen.

Figure 8:
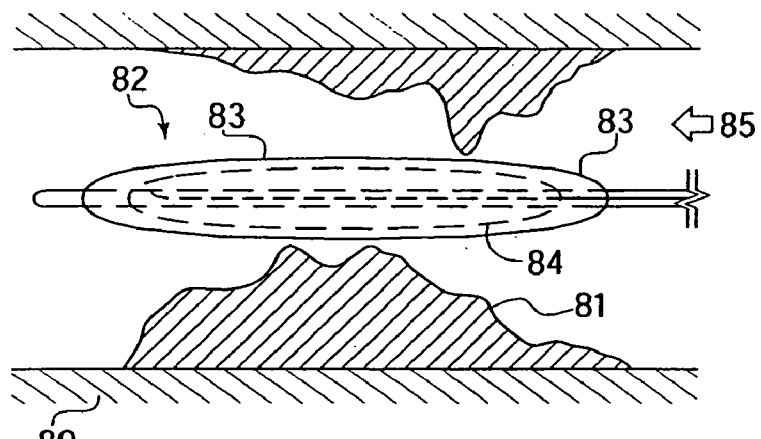
FIG. 8 is a side view of the distal end of a catheter located near an irregular surface of a lumen in accordance with another alternative embodiment of the present invention.

FIGS. 8–11 illustrate the various steps that may be employed in utilizing an alternative embodiment of the present invention. As can be seen in FIG. 8, the distal end of a catheter 82 has been inserted into a vessel 80. This vessel 80 contains irregular lumen walls 81. The arrow 85 in FIG. 8 illustrates the direction in which the catheter 82 has been inserted into the vessel 80. Also evident in FIG. 8 are the balloon 83 and the dilation bladder 84, both located at the distal end of the catheter 82.

Figure 9:
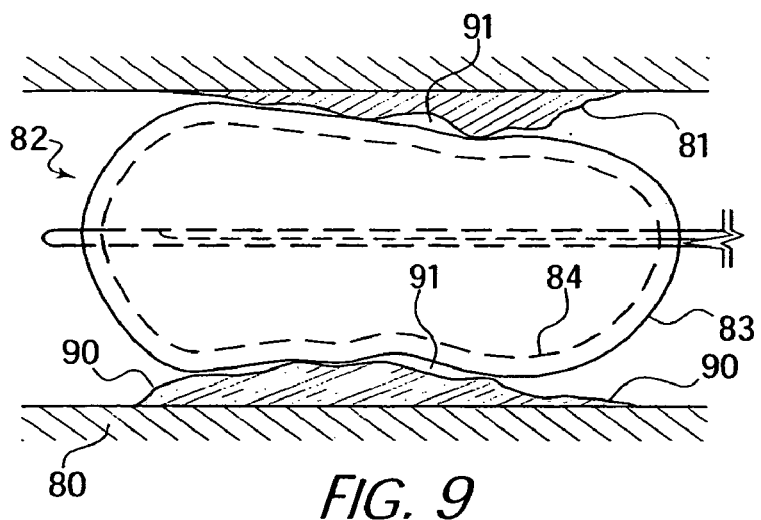
FIG. 9 is a side view of the distal end of the catheter from FIG. 8 illustrating the dilation bladder and the hyper-deformable balloon in an expanded state.

During an initial step illustrated in FIG. 9, the dilation bladder 84 may be inflated by injecting fluid down the catheter 82, thereby enlarging the dilation bladder 84. As can be seen, as the dilation bladder enlarges, so, too, does the balloon 83, whereby both the enlarged balloon and the enlarged bladder swell to meet the irregular lumen wall 81. Due to the structural rigidity of the bladder 84, the previously narrow and highly irregular lumen wall 81 has been smoothed over and dilated by the forces exerted from the bladder 84 to the wall 81. As can be seen in FIG. 9, due to the rigidity of the bladder 84, spaces 91 exist between the balloon 83 and the irregular lumen wall 81 while the bladder 84 is in an expanded state. Also evident in FIG. 9 are uncontacted areas 90 and voids 91 wherein the balloon 83 has not come in contact with the irregular lumen wall 81 at all.

These uncontacted areas 90 and voids 91 form, because the bladder 84, used to dilate the vessel 80 and compact the irregular lumen walls 81, is a rigid and partially flexible material. The material from which the bladder 84 is made may be non-compliant, semi-compliant or compliant but should be rigid enough such that when the dilating bladder 84 is inflated it may dilate the lumen in which it is placed.

Figure 10:
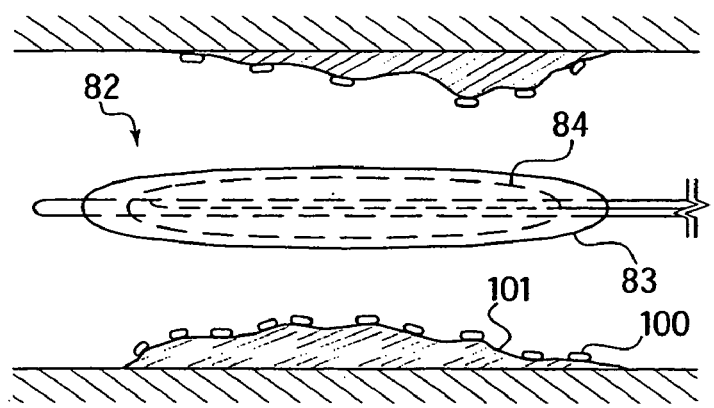
FIG. 10 is a side view of the distal end of the catheter from FIG. 8 after the dilation bladder and hyper-deformable balloon illustrated in FIG. 9 have been deflated.

In FIG. 10, the dilation bladder 84 has been shrunk by extracting the fluid used to expand it through a suction force generated at the proximal end of the catheter 82. This suction force may be generated by pulling on a plunger attached to the syringe, through a vacuum pump located at the proximal end of the catheter 82 or through any other suitable means. As can be seen in FIG. 10, the balloon 83 did not contact the entire surface of the irregular lumen wall 81 as made evident by non-contact points 101 which are illustrated in this figure. Conversely, the balloon did contact some points of the lumen wall, these contact points 100 are identified in FIG. 10. As suggested by their name, they indicate where the balloon 83 contacted the irregular lumen wall 81 during expansion of the bladder 84.

Figure 11:
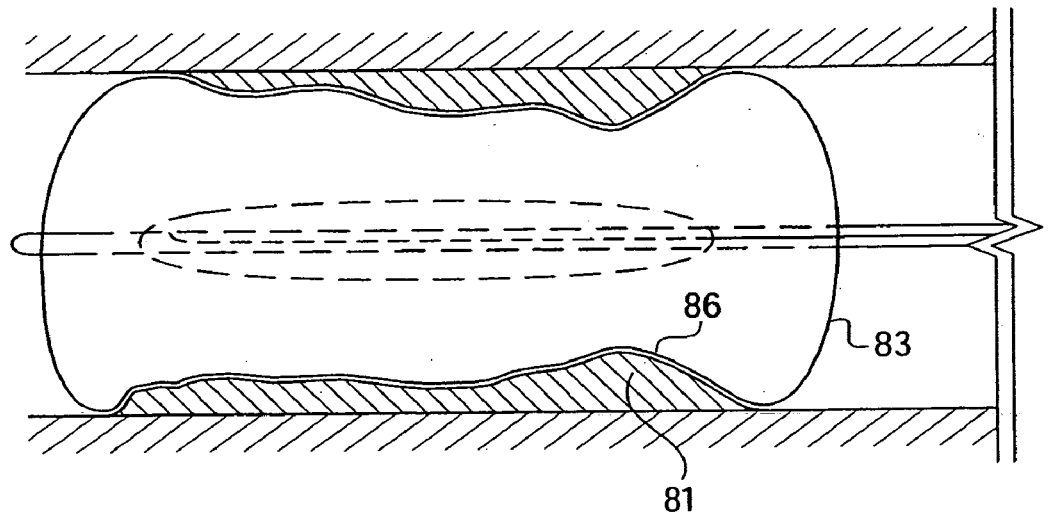
FIG. 11 is a side view of the distal end of the catheter from FIG. 8 illustrating the hyper-deformable inflatable balloon in an inflated state.

In FIG. 11, the balloon 83 has been inflated through the injection of fluid down the catheter under a pressure generated in a pump or other inflation device located at the proximal end of the catheter (which is not shown). As can be seen in FIG. 11, the balloon 83, which is hyper-deformable, has expanded and comes in complete contact with the irregularly shaped lumen wall 81 in this embodiment. This is advantageous because therapeutic 86 located on the outside surface of the balloon 83 may be maintained against the entire surface of the irregular lumen wall 81 while the balloon 83 remains in its expanded state.

With each of the previous embodiments, the therapeutic has been placed or coated on the exterior surface of the inflatable balloon. Alternatively, as suggested above and as described in the following embodiments, the therapeutic may also be located within the inflatable balloon and then forced out through the inflatable balloon to its exterior surface through orifices located in the inflatable balloon or, alternatively, through the balloon itself because the therapeutic may itself be permeable relative to the material comprising the balloon.

Figure 12:
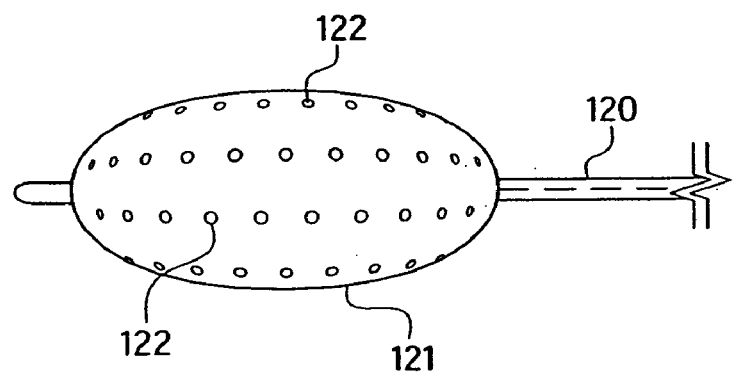
FIG. 12 is a side view of the distal end of a catheter in accordance with another alternative embodiment of the present invention.

FIG. 12 illustrates the distal end of a catheter 120 in accordance with an alternative embodiment of the present invention. This catheter 120 has a first balloon 121 located at its distal end, the first balloon 121 contains a plurality of orifices 122. As mentioned above and as described below, the therapeutic in this embodiment may be located within the first balloon 121 and may be squeezed to its surface after the balloon has been located at the target site within the lumen.

Figure 13:
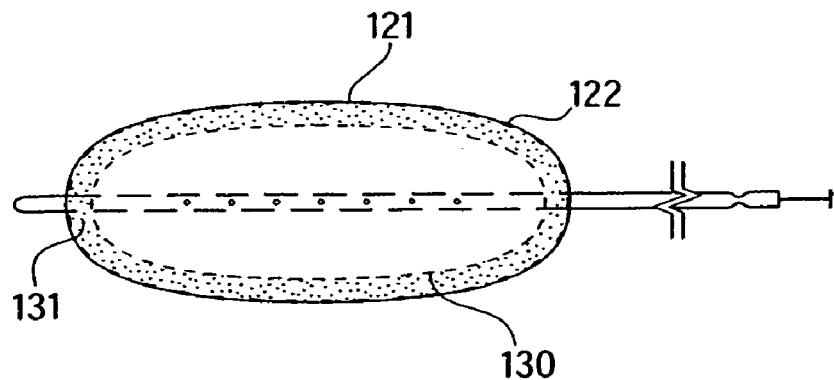
FIG. 13 is a side view of the catheter from FIG. 12.

FIG. 13 is a side view of the catheter from FIG. 12 showing the internal components of the balloon 121. As can be seen, the balloon 121, which contains a plurality of orifices 122, also contains a second balloon 130 and a layer of therapeutic 131 positioned between the surface of the second balloon 130 and the balloon 121.

In use, the embodiment illustrated in FIGS. 12 and 13 may be inserted into an irregularly shaped lumen as described above. Then, as required, the second internal balloon 130 may be inflated, first forcing the first balloon 121 up against the lumen wall and then forcing the therapeutic 131 out through the orifices 122 such that the therapeutic 131 may come in contact with the entire surface of the irregularly shaped lumen wall. An advantage of this configuration is that the therapeutic is not located on the outside of the first balloon and, therefore, is less at risk of becoming errantly placed at a non-target area of the lumen as the catheter is positioned within the body. Alternatively, in another embodiment, rather than having the therapeutic resident on the surface of the inner second balloon, it may, instead, be pumped between the two balloons, from the catheter, during the performance of the procedure.

Figure 14:
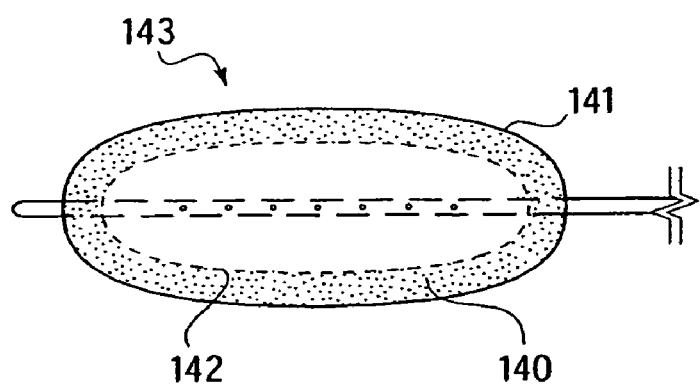
FIG. 14 is a side view of the distal end of a catheter in accordance with another alternative embodiment of the present invention.

The embodiment illustrated in FIG. 14 is similar to the alternative embodiments illustrated in FIGS. 12 and 13. FIG. 14 illustrates the distal end of a catheter 143 in accordance with another alternative embodiment of the present invention. In the alternative embodiment of FIG. 14, rather than having orifices 122 described in the above embodiment, the balloon 141 is manufactured with a material that is permeable to the therapeutic 140 which is located between the second balloon 142 and the first balloon 141. As the second balloon 142 is inflated and the first balloon 141 comes in contact with and rests up against the irregularly shaped lumen surface, the therapeutic 140, resident between the two balloons, may be squeezed through the permeable membrane of the first balloon 141, out onto the exterior surface of the balloon, and in contact with the irregularly shaped lumen wall.

Figure 15:
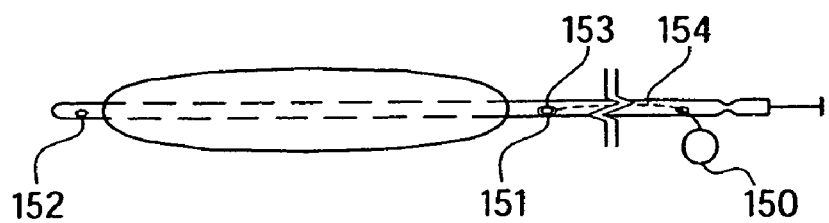
FIG. 15 is a side view of a catheter in accordance with another alternative embodiment of the present invention.

FIG. 15 is a side view of a catheter in accordance with another alternative embodiment of the present invention. The catheter in this embodiment contains an exit orifice 152, an entrance orifice 151, a slide cover 153, a pull ring 150, and a string 154. The exit orifice 152 and the entrance orifice 151 may be fluidly connected within the catheter by a channel or lumen. When the catheter in FIG. 15 is used within an artery or vein of the body, and when the balloon has been inflated, thereby allowing therapeutic to be placed up against the wall of either of these lumens, the slide 153 may be slid open by pulling on the ring 150—allowing blood to flow from the entrance orifice 151, through the lumen within the catheter, and out the exit orifice 152. By allowing blood to flow through the catheter as the catheter is applying therapeutic to the target area, the catheter may be retained in place for a longer period of time. This is especially preferred when the catheter is used in various procedures involving vessels located within the torso of a patient.

The term "therapeutic" as used throughout includes one or more "therapeutic agents" or "drugs." The terms "therapeutic" and "drugs" are used interchangeably herein and include pharmaceutically active compounds, nucleic acids with and without carrier vectors such as lipids, compacting agents (such as histones), virus (such as adenovirus, andenoassociated virus, retrovirus, lentivirus and α-virus), polymers, hyaluronic acid, proteins, cells and the like, with or without targeting sequences. The therapeutics administered in accordance with the invention includes the therapeutic agent(s) and solutions thereof.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

The therapeutic and the delivery balloon may be used, for example, in any application for treating, preventing, or otherwise affecting the course of a disease or tissue or organ dysfunction. For example, the methods of the invention can be used to induce or inhibit angiogenesis, as desired, to prevent or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

A therapeutic delivery balloon is provided. In addition to the embodiments described above, one of skill in the art will realize that these examples are merely illustrative as numerous other embodiments may be implemented without departing from the spirit and scope of the present invention.

What is claimed is:

1. A system for delivering therapeutic to an irregular interior vessel surface comprising:
   a catheter having a proximal end, a distal end, and a first internal lumen;
   a source of fluid in communication with the first internal lumen of the catheter; and
   a first inflatable balloon having an exterior surface and an interior surface,
      the first inflatable balloon attached to the distal end of the catheter and in fluid communication with the first internal lumen of the catheter,
      the first inflatable balloon having a measurable elasticity,
      the exterior surface of the first inflatable balloon at least partially covered with a therapeutic when the first inflatable balloon is in an initial unexpanded state,
      the interior surface of the first inflatable balloon free from contact with the therapeutic when the exterior surface of the first inflatable balloon is at least partially covered with the therapeutic when the first inflatable balloon is in an initial unexpanded state,
      the exterior surface of the first inflatable balloon at least partially covered with a therapeutic when the first inflatable balloon is in an expanded state; and
   a dilation bladder located within the first inflatable balloon,
      the dilation bladder attached to the distal end of the catheter and in fluid communication with a second internal lumen of the catheter by way of a dilation bladder opening in the catheter, the dilation bladder deformable from a non-inflated position to an inflated position, the dilation bladder having a measurable elasticity, the elasticity of the first inflatable balloon being greater than the elasticity of the dilation bladder.

2. The system for delivering therapeutic of claim 1 wherein the exterior surface of the first inflatable balloon is contacting a therapeutic when the first inflatable balloon is in an initial unexpanded state.

3. The system for delivering therapeutic of claim 1 further comprising:

a source of therapeutic, the source of therapeutic in fluid communication with the exterior surface of the first inflatable balloon.

4. The system for delivering therapeutic of claim 1 wherein the first inflatable balloon is made with a latex material and wherein the source of fluid is adapted to control the rate of inflation of the balloon.

5. The system for delivering therapeutic of claim 1 wherein the first inflatable balloon is made with a silicone material and wherein the source of fluid is adapted to control the rate of inflation of the balloon.

6. The system for delivering therapeutic of claim 1 wherein the first inflatable balloon is made with a polyurethane material and wherein the source of fluid is adapted to control the rate of inflation of the balloon.

7. A device for delivering therapeutic to an irregular interior vessel surface comprising:

a catheter having a proximal end, a distal end, and an internal lumen;

a first inflatable balloon attached to the distal end of the catheter and in fluid communication with the internal lumen of the catheter, the first inflatable balloon having a measurable elasticity, the first inflatable balloon having an exterior surface and an interior surface, the exterior surface of the first inflatable balloon at least partially covered with a therapeutic, the first inflatable balloon being impervious to the therapeutic; and a dilation bladder located within the first inflatable balloon, the dilation bladder attached to the distal end of the catheter and in fluid communication with a second internal lumen of the catheter by way of a dilation bladder opening in the catheter, the dilation bladder deformable from a non-inflated position to an inflated position.

8. The device of claim 7 further comprising:

a source of therapeutic, the source of therapeutic in fluid communication with the exterior surface of the first inflatable balloon.

9. A method for delivering therapeutic to an irregular interior vessel surface of a patient comprising:

inserting an expandable first membrane attached to a distal end of a catheter into the vessel of the patient, the expandable first membrane having an exterior surface in contact with therapeutic and having a measurable elasticity;

positioning the expandable first membrane at the irregular interior vessel surface within the patient;

forcing a fluid into the expandable first membrane after positioning the expandable first membrane at the irregular interior vessel surface to inflate the expandable first membrane, the expandable first membrane becoming juxtaposed to and replicating the irregular interior surface of the vessel of the patient; and, after positioning the expandable first membrane at the irregular interior surface of the vessel within the patient, inflating a dilation bladder located within the expandable first membrane, the dilation bladder having a measurable elasticity, the elasticity of the first inflatable balloon being greater than the elasticity of the dilation bladder, the dilation bladder attached to the distal end of the catheter.

10. The method of claim 9 wherein the exterior surface of the expandable first membrane is impervious to therapeutic.

11. The method of claim 9 wherein the fluid is a tracing fluid.

12. The method of claim 9 further comprising:

measuring the volume of fluid forced into the expandable membrane.

* * * * *

UNITED STATES PATENT AND TRADEMARK OFFICE
CERTIFICATE OF CORRECTION

PATENT NO. : 7,179,251 B2
APPLICATION NO. : 09/760807
DATED : February 20, 2007
INVENTOR(S) : Maria Palasis It is certified that error appears in the above-identified patent and that said Letters Patent is hereby corrected as shown below:

Col. 1, line 22, change "shaped" to -- shape, --.

Col. 3, line 49, change "heart," to -- heart; --.
    Line 57, change "livers," to -- liver, --.

Col. 4, line 34, change "inflated" to -- inflated, --.
    Line 59, change "fluid" to -- fluid, --.

Col. 5, line 65, change "601" to -- 601, --.

Col. 6, lines 2 and 3, change "distillation bladder" to -- dilation bladder --.

Col. 7, line 9, change "wall," to -- wall; --.
    Line 37, change "end," to -- end; --.

Col. 8, line 37, change "virus" to -- viruses --.
    Line 41, change "includes" to -- include --.
    Lines 56 and 57, change "viral, liposomes" to -- viral liposomes --.

Col. 9, line 13, change "nitorfurantoin" to -- nitrofurantoin --.
    Line 15, change "lisidomine" to -- linsidomine --.
    Line 21, change "Warafin" to -- Warfarin --.
    Line 24, change "promotors" to -- promoters --.
    Line 26, change "promotors;" to -- promoters; --.
    Line 34, change "endogeneus vascoactive" to -- endogenous vasoactive --.

UNITED STATES PATENT AND TRADEMARK OFFICE
CERTIFICATE OF CORRECTION

PATENT NO. : 7,179,251 B2
APPLICATION NO. : 09/760807
DATED : February 20, 2007
INVENTOR(S) : Maria Palasis It is certified that error appears in the above-identified patent and that said Letters Patent is hereby corrected as shown below:

Col. 10, line 8, change ("BMP's"). to -- ("BMPs"). --.
    Line 12, change "BMP's" to -- BMPs --.
    Line 19, change "DNA's" to -- DNAs --.

Signed and Sealed this

Thirtieth Day of September, 2008

JON W. DUDAS
*Director of the United States Patent and Trademark Office*